United States Patent
Maur et al.

(10) Patent No.: US 12,115,017 B2
(45) Date of Patent: Oct. 15, 2024

(54) METHOD OF CALIBRATING X-RAY PROJECTION GEOMETRY IN X-RAY CONE BEAM COMPUTED TOMOGRAPHY

(71) Applicant: DENTSPLY SIRONA Inc., York, PA (US)

(72) Inventors: Susanne Maur, Bensheim (DE); Stefan Wundrak, Bensheim (DE)

(73) Assignee: DENTSPLY SIRONA INC., York, PA (US)

( * ) Notice: Subject to any disclaimer, the term of this patent is extended or adjusted under 35 U.S.C. 154(b) by 324 days.

(21) Appl. No.: 17/602,306

(22) PCT Filed: Apr. 17, 2020

(86) PCT No.: PCT/EP2020/060825
§ 371 (c)(1),
(2) Date: Oct. 8, 2021

(87) PCT Pub. No.: WO2020/212557
PCT Pub. Date: Oct. 22, 2020

(65) Prior Publication Data
US 2022/0160323 A1  May 26, 2022

(30) Foreign Application Priority Data
Apr. 18, 2019  (EP) .................................. 19170292

(51) Int. Cl.
*A61B 6/58*  (2024.01)
*A61B 6/00*  (2024.01)
(Continued)

(52) U.S. Cl.
CPC ............. *A61B 6/583* (2013.01); *A61B 6/032* (2013.01); *A61B 6/4085* (2013.01); *A61B 6/51* (2024.01);
(Continued)

(58) Field of Classification Search
CPC ....... A61B 6/032; A61B 6/5258; A61B 6/582; A61B 6/12; A61B 6/14; A61B 6/4085;
(Continued)

(56) References Cited

U.S. PATENT DOCUMENTS

| 11,321,833 B2 * | 5/2022 | Kunze ..................... G06T 7/136 |
| 2004/0041807 A1 | 3/2004 | Hornegger |

(Continued)

FOREIGN PATENT DOCUMENTS

| DE | 102011076338 A1 | 11/2012 |
| JP | 2004301860 A | 10/2004 |

(Continued)

OTHER PUBLICATIONS

Gross Daniel et al: "Auto calibration of a cone-beam-CT", Medical D4 Physics, AIP, Melville, NY, US, vol. 39, No. 10, Oct. 1, 2012 (Oct. 1, 2012), pp. 5959-5970, XP012160628, ISSN: 0094-2405, DOI: 10.1118/1.4739247 [retrieved on Sep. 12, 2012] (Year: 2012).*

(Continued)

*Primary Examiner* — Irakli Kiknadze
(74) *Attorney, Agent, or Firm* — DENTSPLY SIRONA INC.

(57) ABSTRACT

A method of x-ray projection geometry calibration in x-ray cone beam computed tomography, including: at least one step (S1) of obtaining two-dimensional x-ray images or a sinogram of at least a part of an object, generated through relatively rotating around the object a detector and an x-ray source projecting x-rays towards the detector; further including: at least one step (S4) of detecting in the two dimensional x-ray images or the sinogram at least one feature of the object by using a trained artificial intelligence algorithm; and at least one step of creating, based on the detection, calibration information which defines the geometry of the x-ray projection.

10 Claims, 2 Drawing Sheets

(51) Int. Cl.
  *A61B 6/03* (2006.01)
  *A61B 6/40* (2024.01)
  *A61B 6/51* (2024.01)
  *G06T 11/00* (2006.01)

(52) U.S. Cl.
  CPC .......... *A61B 6/5205* (2013.01); *A61B 6/5258* (2013.01); *G06T 11/005* (2013.01); *G06T 2210/41* (2013.01)

(58) Field of Classification Search
  CPC ..... A61B 6/584; A61B 6/5205; A61B 6/5264; A61B 6/583; A61B 6/51; A61B 5/4547; A61B 5/0073; A61B 6/025; A61B 5/725; A61B 6/5247; A61B 2576/02; A61B 2505/05; A61B 6/5217; A61B 6/467; A61B 6/54; A61B 6/463; A61B 6/4441; A61B 6/481; A61B 6/486; A61B 6/487; A61B 6/504; A61B 6/507; A61B 6/5211; A61B 6/5235; A61B 6/4014; A61B 6/4411; A61B 6/5282; G06T 11/005; G06T 2210/41; G06T 7/0012; G06T 2207/10116; G06T 2207/30168; G06T 7/0016; G06T 2207/10016; G06T 2207/10081; G06T 2207/20081; G06T 2207/20084; G06T 2207/30101; G06T 2211/424; G16H 30/40; G16H 20/40; G16H 50/20; G16H 50/50; G16H 50/70; G16H 30/00; G16H 30/20; G16H 40/67; A61N 5/1031; A61N 5/1039; A61N 5/103; A61N 5/1038; A61N 5/1045; A61N 5/1081; A61N 5/1047; A61N 5/1067; A61N 5/1075; G06N 3/08; G06N 3/045; G06N 3/0454; G06N 3/084; G06N 20/10; G06N 3/04; H01S 3/0014; G01M 11/00; A61C 9/0053; G01N 23/046; G01N 2223/419
  USPC ......................................................... 378/207
  See application file for complete search history.

(56) References Cited

U.S. PATENT DOCUMENTS

| 2008/0186311 A1* | 8/2008 | Claus ..................... A61B 6/032 382/181 |
| 2008/0192884 A1 | 8/2008 | Ritter |
| 2018/0368781 A1 | 12/2018 | De Man |
| 2021/0177371 A1* | 6/2021 | Wang ..................... A61B 90/39 |

FOREIGN PATENT DOCUMENTS

| JP | 2005177112 A | 7/2005 |
| JP | 2006288719 A | 10/2006 |
| JP | 2008188426 A | 8/2008 |
| JP | 2016539757 A | 12/2016 |

OTHER PUBLICATIONS

Japanese Office Action dated Feb. 6, 2024.
International Search Report; PCT/EP2020/060825; Jun. 16, 2020 (completed); Jun. 24, 2020 (mailed).
International Preliminary Report on Patentability; PCT/EP2020/060825; Jun. 16, 2020 (completed); Jun. 24, 2020 (mailed).
Written Opinion of the International Searching Authority; PCT/EP2020/060825; Jun. 16, 2020 (completed); Jun. 24, 2020 (mailed).
Gross et al; "Auto Calibration of a cone-beam-CT"; Medical Physics, AIP, Melville, NY; vol. 39, No. 10; Oct. 1, 2012; pp. 5959-5970.
Maier et al; "A gentle introduction to deep learning in medical image processing" Zeitschrift Fuer Medizinishe Physik; vol. 29, No. 2; Jan. 25, 2019; pp. 86-101.
Shijun et al; "Machine learning and radiology"; Medical Image Analysis, Oxford University Press, Oxford GB; vol. 16, No. 5; Feb. 12, 2012; pp. 933-951.

* cited by examiner

METHOD OF CALIBRATING X-RAY PROJECTION GEOMETRY IN X-RAY CONE BEAM COMPUTED TOMOGRAPHY

CROSS-REFERENCE TO RELATED APPLICATIONS

This is a National Phase application of International Application No. PCT/EP2020/060825, filed Apr. 17, 2020, which claims the benefit of and priority to European Application Ser. No. 19170292.7, filed on Apr. 18, 2019, which are herein incorporated by reference for all purposes.

TECHNICAL FIELD OF THE INVENTION

The present invention relates to x-ray volume tomography (VT), particularly to x-ray dental volume tomography (DVT). The present invention more particularly relates to a method of calibrating x-ray projection geometry in x-ray volume tomography. The present invention more particularly relates to motion artefact reduction in x-ray volume tomography. The present invention more particularly relates to x-ray cone beam computed tomography (CBCT).

BACKGROUND ART OF THE INVENTION

In a system for x-ray cone beam computed tomography, a sensor and a detector are relatively rotated around a patient, particularly around the patient's head to generate a plurality of projection images i.e., two-dimensional (2D) x-ray images. To calculate a three-dimensional (3D) tomographic image from these 2D x-ray images, knowledge of the projection geometry of each 2D x-ray images is required. The calibration of the projection geometry of the x-ray CBCT system is usually performed at the factory or after installation of the x-ray CBCT system in the doctor's office. For this purpose, 2D x-ray images are generated with a calibration body. A calibration body has a predefined shape and one or more features that are easy to detect and identify in the 2D x-ray images. In addition, the relative locations of the features are generally known. By applying so-called consistency conditions to the 2D x-ray images, the projection geometry of the 2D x-ray images can be derived. Reference is made to the paper "Auto-calibration by locally consistent contours for dental CBCT, S. Maur et al 2018 Phys. Med. Boil. 63 215018. The projection geometry forms the basis of the calibration information of the x-ray CBCT system. Mechanical changes such as motions and/or deformations or the like in the x-ray CBCT system relative to the irradiated patient can invalidate the calibration information. For instance, a relative movement of the patient during the acquisition of the 2D x-ray images result in the calibration information of the x-ray CBCT system to become incorrect. For a correct reconstruction of a 3D tomographic image, the projection geometry is relevant relative to the patient, and not relative to a fixed point in the room such as the calibration body. If the patient moves during the acquisition, the assumed x-ray projection geometry does not match the acquired 2D x-ray images. This leads to a data inconsistency in the reconstruction of the 3D tomographic image. Hence, this further causes motion artifacts in 3D tomographic image such as blurred structures and/or double edges. Therefore, in the prior art, auto-calibration methods have been envisaged to create calibration information for the 2D x-ray images. However, these are still the subject matter of research and development. In such methods of auto-calibration, any part of the patient may be used as a feature for calibration, for example, the anatomical parts of the patient can be used. However, since the shape, location and density of these features are generally unknown, the accurate detection thereof in the 2D x-ray images is difficult. The feature detection is complicated due to the many overlapping anatomical parts as well as the low contrast and the high image noise at low x-ray dose. Hence, the information content of the individual projection images is usually not enough for accurate feature detection. To increase the accuracy, prior knowledge might be integrated into the feature detection. For example, prior knowledge may relate to the shape, location, and density of the anatomical parts. The prior knowledge may further relate to assumptions about the movement of the patient or the x-ray CBCT system. However, the full modeling of such prior knowledge and its integration into the feature detection algorithms is not trivial, and it is difficult to achieve high accuracy and completeness. This makes the image processing for detecting the features in the 2D x-ray images to become very slow and prone to errors, and thus the accuracy of the calibration information and the speed of the auto-calibration process are adversely affected.

SUMMARY OF THE INVENTION

An objective of the present invention is to overcome the above-mentioned disadvantages of the prior art and to provide a method of projection geometry calibration in x-ray cone beam computed tomography.

The present invention provides a method of x-ray projection geometry calibration in x-ray cone beam computed tomography. The method comprises at least one step of obtaining two-dimensional x-ray images or a sinogram of at least a part of an object, generated through relatively rotating around the object a detector and an x-ray source projecting x-rays towards the detector; at least one step of detecting in at least part of the two dimensional x-ray images or the sinogram a feature of the object by using a trained artificial intelligence algorithm; and at least one step of creating, based on the detection, calibration information which defines the geometry of the x-ray projection.

A major advantageous effect of the present invention is the application of the trained artificial intelligence algorithm for feature detection in the 2D x-ray images or the sinogram for calibrating the x-ray projection geometry. The artificial intelligence algorithm learns implicit knowledge about the 2D/3D location, shape and also the density of the anatomical parts as well as the consistency conditions of the data, and the effects of the typical motion of the patient and the x-ray CBCT system. This learning makes the artificial intelligence algorithms more accurate and much faster than classical image processing. Hence, the motion artefacts in the 3D tomographic image can be more effectively reduced, and a sharp 3D tomographic image can be obtained.

According to the present invention, the features of the object in the 2D x-ray images or the sinogram may be detected through 2D or 3D masks that are generated by the trained artificial intelligence algorithm. The 2D or 3D masks represent the location/shape, and particularly the contours or the silhouettes of the features. The 2D and 3D masks may be binary masks. Alternatively, probability masks or confidence masks may be used.

According to the present invention, the calibration information created may be an x-ray unit-specific calibration information or a patient-specific calibration information. The x-ray unit-specific calibration information can be created by irradiating a calibration body such as a dummy. A patient-specific calibration information can be created by irradiating the patient. The features of the patient to be detected may correspond to anatomical parts or prosthetic parts. The anatomical part may be a tooth or a bone. And the prosthetic part may be an implant, a crown, or a filling and the like.

According to the present invention, the x-ray unit-specific calibration information for the x-ray CBCT system may be created at the factory when it is manufactured, and subsequently temporarily or permanently stored in the x-ray CBCT system. Alternatively, the x-ray unit-specific calibration information may be created during the installation and optionally at predetermined intervals following the installation and similarly stored in the x-ray CBCT system. The x-ray unit-specific calibration information may also be created and stored when artefacts are observed in the computed tomography. The patient-specific calibration information for the x-ray CBCT system may be separately created for each patient, and subsequently stored for use when reconstructing the respective patient's volume tomographic image.

According to the present invention, various patient-specific calibration information of different patients may be created, stored and compared with the x-ray-unit specific calibration unit to analyze the mismatch and to draw conclusions on the correctness of the x-ray-unit specific calibration or the motional behavior of the patient. An incorrect x-ray unit specific calibration information may be automatically adjusted based on the analysis. Alternatively, the user may be informed on the fault in the x-ray-unit specific calibration information through displaying fault information on a control display or on a display of the reconstructed 3D tomographic image to initiate the creation of a new calibration information. Alternatively, the user may be informed through a speaker. Alternatively, the user may be similarly informed on the motional behavior of the patient, preferably when such motion is excessive, and the motion artefacts cannot be satisfactorily reduced.

According to the present invention, a previously stored x-ray unit-specific calibration information may be updated with a recently created x-ray unit-specific calibration information. Similarly, a previously stored patient-specific calibration information may be updated with a recently created patient-specific calibration information corresponding to the same patient.

According to the present invention, a three-dimensional tomographic image of at least a part of the body of a patient may be reconstructed using the x-ray unit-specific calibration or alternatively the corresponding patient-specific calibration information.

According to the present invention, the two-dimensional x-ray images or the sinogram may be optionally pre-processed prior to the detection step through image processing based on a trained artificial intelligence algorithm or a classical algorithm. The image processing algorithm may at least include a filtering process, a contrast enhancement process, an edge enhancement process, and a noise suppression process.

According to the present invention, one or more, or even all features to be detected can be automatically selected or alternatively manually selected through the user on a display.

According to the present invention, the artificial intelligence algorithm for detecting the features is trained preferably by using data pairs. Each data pair includes a two-dimensional x-ray image and an associated 2D mask which represents the 2D location and/or shape of a feature in the associated two-dimensional x-ray image. Alternatively, each data pair includes a sinogram and an associated 3D mask which represents the 3D location and/or shape of a feature in the sinogram. These data pairs may be generated through a robotic motion of a real calibration body in a lab. Alternatively, these data pairs may be obtained from various patients. Alternatively, the data pairs may be virtually generated through a simulation.

The present invention also provides an x-ray volume tomography system, preferably an x-ray cone beam computed tomography system. The x-ray cone beam computed tomography system comprises an x-ray unit which has a generating means for generating two-dimensional x-ray images or a sinogram of at least a part of an object, through relatively rotating around the object a detector and an x-ray source for projecting x-rays towards the detector. The object may be a calibration body such as a dummy or a patient, preferably the head of the patient, more preferably the jaw of the patient. The x-ray volume tomography system further comprises a tomographic reconstruction unit which has an image processing means adapted to execute the steps of the x-ray projection geometry calibration method of the present invention.

The present invention also provides a computer-readable program comprising codes for causing a computer-based x-ray volume tomography system to perform the method steps of the present invention. The computer-readable program may be provided together with an x-ray volume tomography system or on a computer-readable storage.

BRIEF DESCRIPTION OF THE DRAWINGS

In the subsequent description, the present invention will be described in more detail by using exemplary embodiments and by referring to the drawings, wherein FIG. 1—is a flowchart showing the steps of a method of x-ray projection geometry calibration in x-ray cone beam computed tomography according to the present invention.

DETAILED DESCRIPTION OF THE INVENTION

Figure 1:
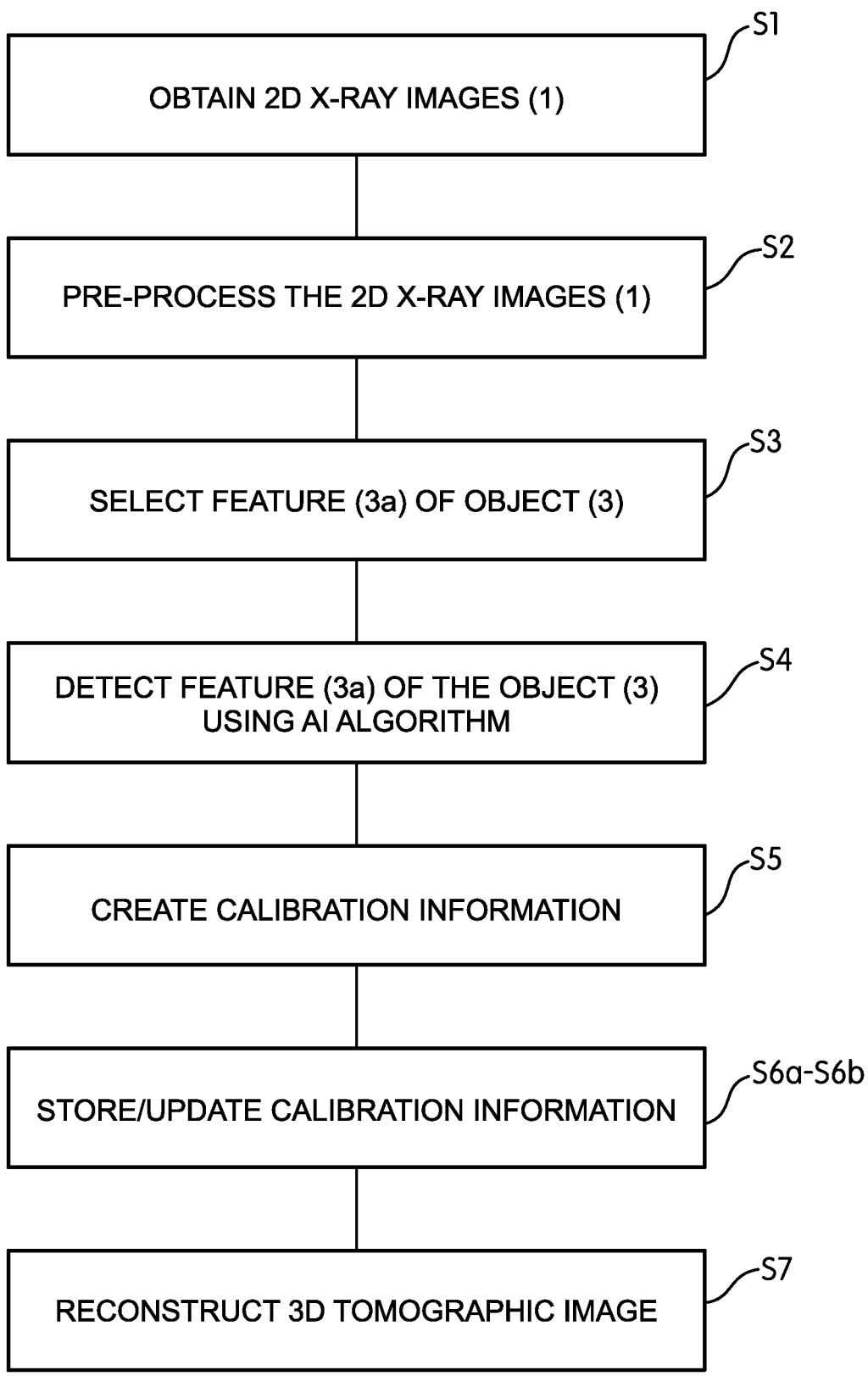

The reference numbers shown in the drawings denote the elements as listed below and will be referred to in the subsequent description of the exemplary embodiments.

1. 2D x-ray image
2. Sinogram
3. Object (e.g. Patient or calibration body)
3a. Feature (e.g. Anatomical/Prosthetic Part)
3b. Location/Shape FIG. 1 shows the steps (S1-S7) of the x-ray projection geometry calibration method for x-ray cone beam computed tomography according to an embodiment of the present invention.

In a first step (S1), a plurality two-dimensional x-ray images (1) or a sinogram (2) of at least a part of an object (3) is obtained from an x-ray cone beam computed tomography system of the present invention. The object (3) may be a patient or a calibration body such as a dummy. The three-dimensional x-ray images (1) and the sinogram (2) are generated by the x-ray cone beam computed tomography system through relatively rotating around the object (3) a detector and an x-ray source projecting x-rays towards the detector.

In an optional second step (S2), the two-dimensional x-ray images (1) or the sinogram (2) is pre-processed. The pre-processing step (S2) comprises at least one of a filtering process, a contrast enhancement process, an edge enhancement process, and a noise suppression process.

In another optional third step (S3), one or more features (3a) of the object (3) are selected in the 2D x-ray images (1) or the sinogram (2) as originally obtained or as pre-processed. The selection can be performed manually on a display. Alternatively, the selection is performed automatically.

Figure 2:
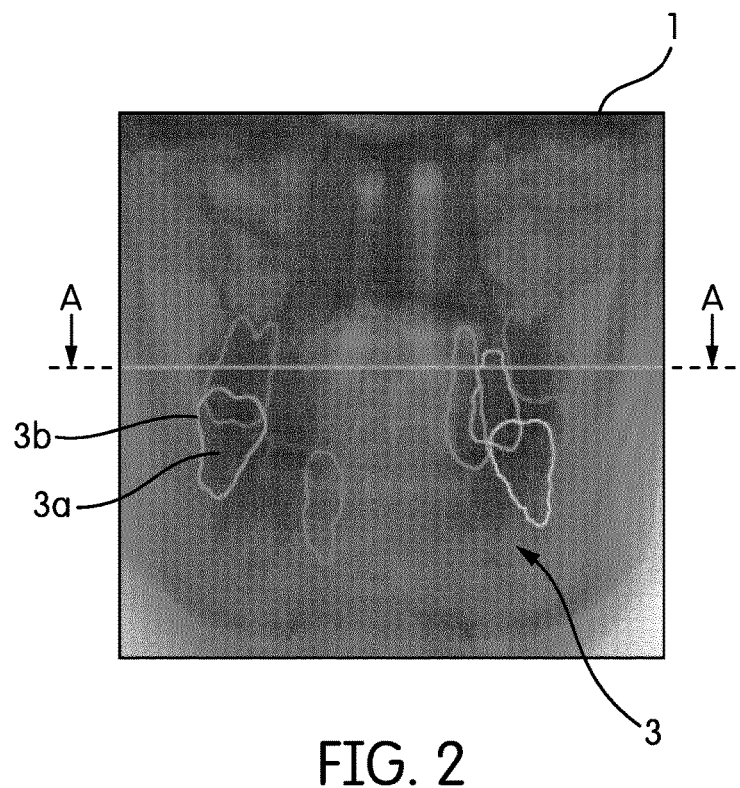
FIG. 2—is a two-dimensional x-ray image generated through an x-ray unit according to the present invention.
Figure 3:
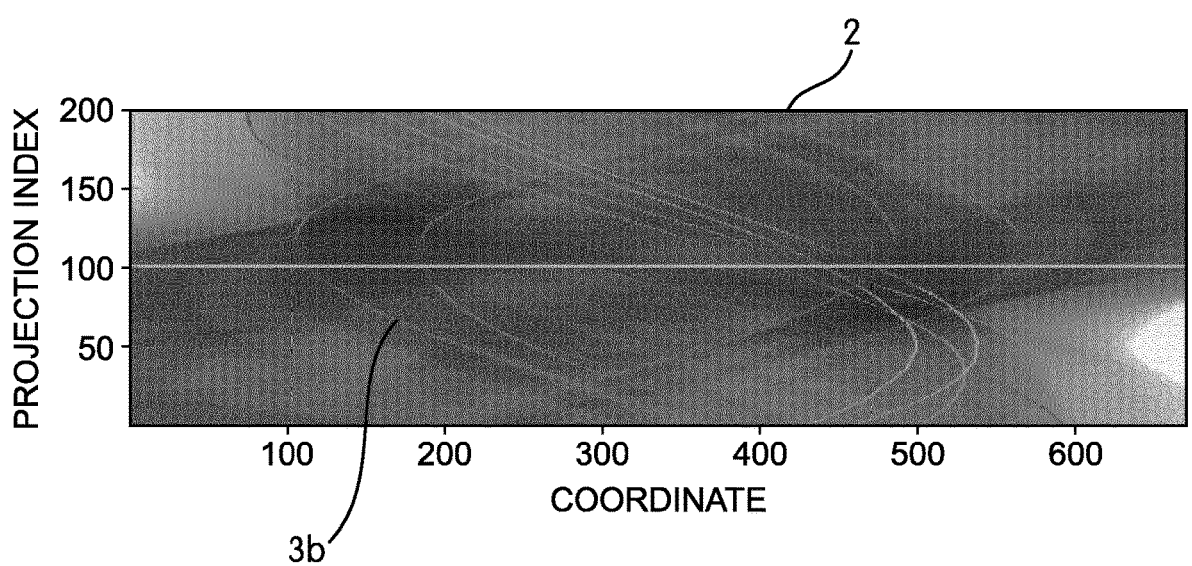
FIG. 3—is a cross sectional view of a sinogram, along the line A-A in FIG. 2, of the two-dimensional x-ray images generated through the x-ray unit according to the present invention.

In a fourth step (S4), at least one feature (3a), optionally the selected feature (3a) of the object (3) is detected in the two-dimensional x-ray images (1) or the sinogram (2), or optionally in the pre-processed two-dimensional x-ray images (1) or the pre-processed sinogram (2) by using a trained artificial intelligence algorithm. Optionally additional information may be input into the trained artificial intelligence algorithm for detecting the feature (3a) in the fourth step (S4). The additional information may include an initial estimation about the 2D/3D position, shape and relative motion of the feature (3a). The additional information may include information to enhance detection of the at least one selected feature (3a) of step (S3). The feature (3a) may be detected simultaneously or one after the other. A further pre-processing step can be optionally performed after the selection step (S3). Thereby, for instance the pre-processing can be adapted to the spatial or image properties of the selected feature (3a) to optimize the feature detection. The feature (3a) to be detected may correspond to an anatomical part or a prosthetic part of the patient, particularly of the patient head, more particularly of the patient jaw. The anatomical part might be a tooth or a bone or the like. The prosthetic part might be an implant or the like. As shown in FIG. 2, the trained artificial intelligence algorithm generates 2D masks which represent the 2D location and/or 2D shape (3b) of the feature (3a) of the object (3) i.e., the tooth in the patient's jaw, in the two-dimensional x-ray images (1). FIG. 3 is a cross sectional view of the sinogram (2), along the line A-A in FIG. 2, that includes the two-dimensional x-ray image (1) of FIG. 2 at the projection index "100". The projection index and the coordinates may vary depending on the details of the tomography. The projection index indicates the plurality of two-dimensional x-ray images (1) in the sinogram (2). As shown in FIG. 3, the trained artificial intelligence algorithm may alternatively generate a 3D mask which represents the 3D location and/or 3D shape (3b) of the feature (3a) of the object (3) i.e., the tooth in the patient's jaw, in the sinogram (2). In the subsequent description, the reference signs which have a prime denote elements that are used for training the artificial intelligence algorithm. The artificial intelligence algorithm is trained using data pairs. Each data pair includes a two-dimensional x-ray image (1') and an associated 2D mask which represents the location and/or shape (3b') of a feature (3a') in the associated two-dimensional x-ray image (1). Alternatively, each data pair includes a sinogram (2') and an associated 3D mask which represents the location and/or shape (3b') of a feature (3a') in the sinogram (2).

In a fifth step (S5), based on the detection, calibration information is created. The calibration information defines the geometry of the x-ray projection. When the irradiated object (3) is a calibration body, the created calibration information corresponds to an x-ray unit-specific calibration information. When the irradiated object (3) is a patient, the created calibration information corresponds to a patient-specific calibration information.

In an optional initial stage of the sixth step (S6a), the recently created x-ray unit-specific calibration information and the patient-specific calibration information are stored temporarily or permanently in the x-ray cone beam computed tomography system. Various patient-specific calibration information pertaining to different patients may be created and stored. In an optional subsequent stage of the sixth step (S6b) the previously stored x-ray unit-specific calibration information and the previously stored patient-specific calibration information are updated with the recently created x-ray unit-specific calibration information and the recently created patient-specific calibration information of the same patient respectively.

In a seventh step (S7), a three-dimensional tomographic image is reconstructed based on the two-dimensional x-ray images (1) or a sinogram (2) of at least a part of the body of a patient and the x-ray unit-specific calibration. Alternatively, the three-dimensional tomographic image may be reconstructed based on the two-dimensional x-ray images (1) or the sinogram (2) of at least a part of the body of the patient and the corresponding patient-specific calibration information.

The x-ray cone beam computed tomography system of the present invention has an x-ray unit and a tomographic reconstruction unit. The x-ray unit has an acquisition means adapted to acquire two-dimensional x-ray images (1) or the sinogram (2) of at least part of an object (3) through relatively rotating around the object (3) the x-ray source and the detector. The tomographic reconstruction unit has an image processing means adapted to perform the steps of the x-ray projection geometry calibration method.

The method may be provided in form of a computer-readable program having codes for causing the computer-based x-ray cone beam computed tomography system to execute the above described method steps (S1-S7). The computer-readable program may be stored in a computer-readable storage of the computer-based x-ray cone beam computed tomography system.

The invention claimed is:

1. A method of x-ray projection geometry calibration in x-ray cone beam computed tomography, the method comprising:
    obtaining a sinogram of at least part of an object, wherein the sinogram is generated through relatively rotating around the object, a detector and an x-ray source projecting x-rays towards the detector;
    detecting in the sinogram, at least one feature of the object by using a trained artificial intelligence algorithm, wherein
    the object is a patient, and
    the at least one feature of the object includes an anatomical part or a prosthetic of a body or a head of the patient;
    creating, based on the detected sinogram, calibration information which defines a geometry of a x-ray projection, wherein the created calibration information corresponds to a patient-specific calibration information; and
    reconstructing, based on the sinogram of the at least part of the body of the patient and the corresponding patient-specific calibration information, a three-dimensional tomographic image.

2. The method of claim 1, wherein the trained artificial intelligence algorithm generates a 3D mask which represents a 3D location and a 3D shape of the feature of the object in the sinogram.

3. The method of claim 1, wherein the anatomical part comprises at least part of a tooth or a bone, and the prosthetic part comprises at least part of an implant.

4. The method of claim 1, further comprises:
storing a recently created patient-specific calibration information, or
updating a previously stored patient-specific calibration information with the recently created patient-specific calibration information respectively.

5. The method of claim 1, further comprises:
pre-processing the sinogram before detecting the at least one feature of the object in the sinogram.

6. The method of claim 5, wherein the pre-processing the sinogram comprises at least one of a process of filtering, a contrast enhancement, an edge enhancement, and a noise suppression.

7. The method of claim 1, further comprises:
selecting one or more a features to be detected in the sinogram.

8. The method of claim 1, further comprises:
training the artificial intelligence algorithm by using a plurality of data pairs, wherein each data pair of the plurality of data pairs includes a sinogram and an associated 3D mask which represents a 3D location and a 3D shape of a feature in the sinogram.

9. A system for x-ray cone beam computed tomography, comprising:
an x-ray unit comprising an acquisition means adapted to acquire a sinogram of at least part of an object through relatively rotating, around the object, an x-ray source and a detector;
a tomographic reconstruction unit comprising an image processing means adapted to detect in the sinogram, at least one feature of the object by using a trained artificial intelligence algorithm, wherein
the object is a patient, and
the at least one feature of the object includes an anatomical part or a prosthetic of a body or a head of the patient;
create, based on the detected sinogram, calibration information which defines a geometry of a x-ray projection, wherein the created calibration information corresponds to a patient-specific calibration information; and
reconstruct, based on the sinogram of the at least part of the body of the patient and the corresponding patient-specific calibration information, a three-dimensional tomographic image.

10. A non-transitory computer-readable medium storing a program in the medium comprising codes for causing a computer-based x-ray volume tomography system to perform a method of:
obtaining a sinogram of at least part of an object, wherein the sinogram is generated through relatively rotating around the object, a detector and an x-ray source projecting x-rays towards the detector;
detecting in the sinogram, at least one feature of the object by using a trained artificial intelligence algorithm, wherein
the object is a patient, and
the at least one feature of the object includes an anatomical part or a prosthetic of a body or a head of the patient;
creating, based on the detected sinogram, calibration information which defines a geometry of a x-ray projection, wherein the created calibration information corresponds to a patient-specific calibration information; and
reconstructing, based on the sinogram of the at least part of the body of the patient and the corresponding patient-specific calibration information, a three-dimensional tomographic image.

\* \* \* \* \*